US 6,221,674 B1

(12) United States Patent
Sluka et al.

(10) Patent No.: US 6,221,674 B1
(45) Date of Patent: Apr. 24, 2001

(54) PROCESS FOR THE APPLICATION OF REAGENT SPOTS

(75) Inventors: Peter Sluka, Weilheim; Wolfgang Knoll; Manfred Zizlsperger, both of Mainz, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/059,219

(22) Filed: Apr. 13, 1998

(30) Foreign Application Priority Data

Apr. 14, 1997 (DE) .............................. 197 15 484

(51) Int. Cl.$^7$ ........................... G01N 21/75; G01N 33/53
(52) U.S. Cl. ............................ 436/166; 435/973
(58) Field of Search ........................ 436/166; 427/2.11, 427/2.13, 385.5, 387, 388.1; 435/525, 973, 7.2

(56) References Cited

U.S. PATENT DOCUMENTS

| | | | |
|---|---|---|---|
| 5,149,626 | * | 9/1992 | Fleming ................................ 435/973 |
| 5,512,131 | * | 4/1996 | Kumar et al. ...................... 156/655.1 |
| 5,514,501 | * | 5/1996 | Tarlov .................................... 430/5 |
| 5,567,627 | * | 10/1996 | Lehnen ................................ 435/973 |
| 5,620,850 | * | 4/1997 | Bamdad et al. ...................... 530/300 |
| 5,827,748 | * | 10/1998 | Golden ................................. 435/973 |
| 5,837,551 | * | 11/1998 | Ekins .................................... 435/973 |
| 5,858,801 | * | 1/1999 | Brizzolara ............................ 435/973 |
| 5,879,878 | * | 3/1999 | Raguse et al. ........................... 435/4 |
| 5,922,550 | * | 7/1999 | Everhart et al. ..................... 435/7.21 |

FOREIGN PATENT DOCUMENTS

| | | |
|---|---|---|
| 4039677 | 6/1992 | (DE) . |
| 0664452 | 7/1995 | (EP) . |

OTHER PUBLICATIONS

Kumar et al., 'Patterning Self–Assembled Monolayers: Applications in Materials Science', Langmuir 10, 1498–1511, Feb. 1994.*

Huang et al., 'Photopatterning of Self–Assembled Alkanethiolate Monolayers on Gold: A Simple Monolayer Photoresist Utilizing Aqueous Chemistry', Langmuir 10, 626–628, Jan. 1994.*

* cited by examiner

Primary Examiner—Robert J. Warden, Sr.
Assistant Examiner—Theresa T. Snider
(74) Attorney, Agent, or Firm—Fulbright & Jaworski, LLP

(57) ABSTRACT

A process is described for applying spatially defined reagent areas to a solid phase which is characterized in that a liquid containing an adsorptive binding reagent is contacted with spatially defined areas of a solid phase which comprises an essentially continuous metal or metal oxide surface for an adequate time period to enable the formation of adsorptive bonds between the binding reagent and the solid phase.

11 Claims, 6 Drawing Sheets

PROCESS FOR THE APPLICATION OF REAGENT SPOTS

DESCRIPTION

Figure 1:
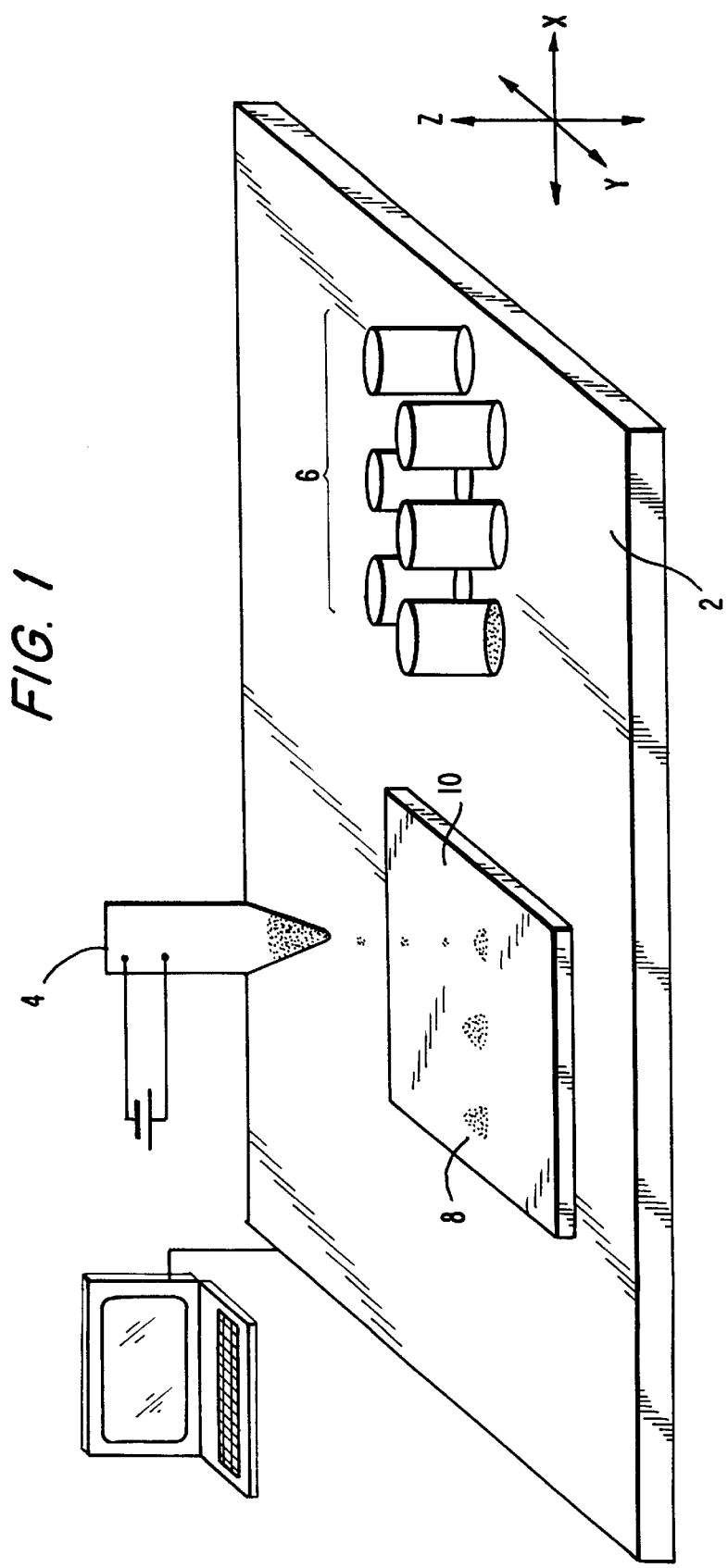
Figure 2A:
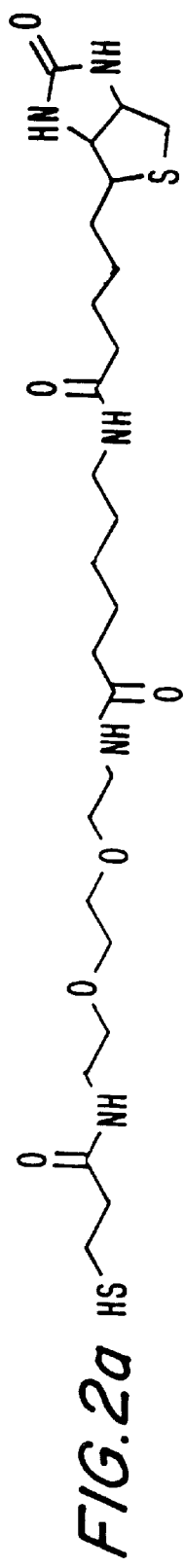
Figure 2B:
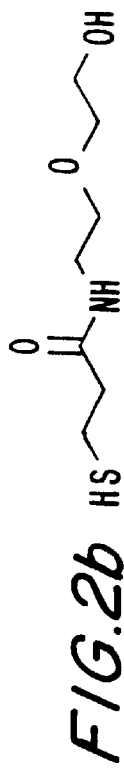
Figure 2C:
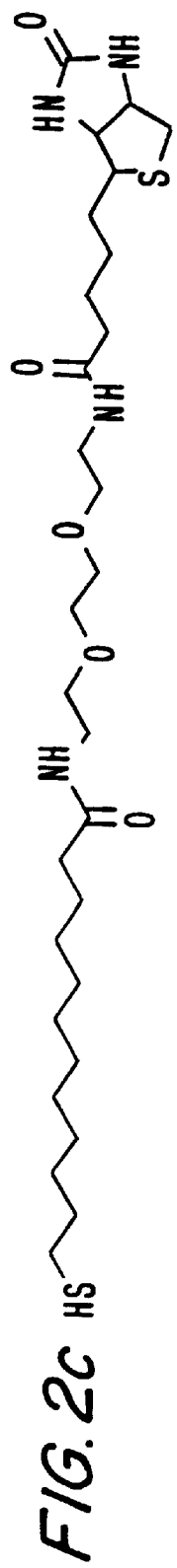
Figure 2D:

The invention concerns a process for applying spatially defined reagent areas or reagent spots on a solid phase with a metal or metal oxide surface and also concerns a solid phase binding matrix which comprises different solid phase reactants or/and solid phase reactants at different concentrations in spatially defined reagent spots.

A number of processes are known which can be used to apply small amounts of reagent to different surfaces such as glass or plastic supports. Such processes lead to a microstructuring of the reagents on the surface e.g. in the form of reagent spots that are spatially separated from one another. Of particular interest in this connection are microstructured surfaces in which the reagent spots each have different functionalities, so-called arrays, in which the individual reagent spots for example contain different reactants such as DNA fragments or antibodies. A process is described in WO 92/10 092 which can be used to generate a plurality of different structures on a glass support by means of photoreactive compounds and irradiation using masks. A process is described in U.S. Pat. No. 4,877,745 in which differently functionalized spots can be applied to plastic supports by means of ink-jet.

In contrast to plastic surfaces, metal and metal oxide surfaces have the advantage that they can be coated with an exactly defined matrix layer by self-assembly techniques. A self-assembled monolayer (SAM) is formed for example when organic alkylthiols are adsorbed onto a gold surface, the spontaneous organisation of such a densely packed monolayer being based on strong specific interactions between the support material and the adsorbent (Nuzzo et al., J. Am. Chem. Soc. 105 (1983) 4481). In this manner it is possible to apply an exactly defined monolayer of a binding matrix to the surface of metals such as e.g. gold or silver. Furthermore the specific binding capability of self-assembled solid phases can be further optimized by dilution of the specific solid phase reactants as described in EP-A-0 515 615.

The coating of metal surfaces with microstructures based on self-assembled monolayers is also known. Thus Whitesides et al., Langmuir 10 (1994) 1498–1511 describe a process in which reagents are stamped onto a noble metal surface by means of a special microstructured silicone stamp. This enables microstructured monolayers to be generated with zones that are spatially separated from one another. However, in such a stamping process individual zones are obtained that are all identically functionalized i.e. it is not possible with this technique to obtain a different functionality by a different coating of individual spots as in an array structure.

Furthermore it is known that microstructures of self-assembled monolayers on noble metal surfaces can be formed by irradiation through masks of substrates whose whole area is covered with thiols and subsequent washing (Hemminger et al., Langmuir 10 (1994), 626–628). Spatially separate zones are also formed in this process which are all identically functionalized. A further possibility of producing reagent spots is firstly to apply gold spots to a support that are already spatially separated from one another which are then subsequently coated with reagents. However, it is time-consuming to manufacture such spatially separated gold spots and they have to be generated by vapour-depositing the substrate through masks. Moreover the subsequent coating of the gold spots with reagents for example with micropipettors requires very precise handling which in the case of structures in the $\mu$m range is very difficult to realise and is technically very complicated.

Therefore the object of the invention was to provide a process with which array structures of reagent spots can be applied in a simple manner to metal or metal oxide surfaces.

This object is achieved according to the invention by a process for applying spatially defined reagent areas to a solid phase which is characterized in that a liquid containing an adsorptive binding reagent is contacted with spatially defined areas of a solid phase which comprises an essentially continuous metal or metal oxide surface for an adequate time period to enable the formation of adsorptive bonds between binding reagent and solid phase.

Surprisingly it was possible to eliminate the disadvantages occurring in the state of the art by spotting the reagents used for self-assembly in one solution directly onto a reagent support coated all over with a metal or a metal oxide. The reagent spots can for example be applied by means of ink-jet methods or with an automatic micropipetting device. In this process the reagent solution is applied to the surface in the form of small droplets preferably in the form of microdroplets.

After applying the reagent solution the surface is incubated for a certain time period e.g. 1 to 60 min, preferably 5 to 10 minutes in order to enable adsorptive bonds to form between the binding reagent and metal or metal oxide surface. The incubation period depends on the binding reagent used and on the surface but the incubation is long enough to enable the formation of adsorptive bonds. In this process a self-assembled monolayer of the binding reagent is formed on the metal or metal oxide surface in the form of spatially defined areas. After incubation the surface is rapidly washed with a large excess of solvent in order to prevent smearing of adjacent zones. Aqueous or/and organic solvents can be used as the solvent depending on the binding reagent used.

Surprisingly it is possible to form spatially defined areas in the form of spots by applying adsorptively binding reagents to a continuous metal or metal oxide layer in which a significant smearing of adjacent reagent spots does not occur during the application or subsequently. Despite the merely adsorptive binding between the surface and binding reagent discrete spots are formed since the adsorptive binding reagent is surprisingly stationary. An important advantage of the process is that surface regions can be produced with different coatings or functionalities that can be used for multiparameter assays in detection methods e.g. in immunological or nucleic acid hybridization assays. Furthermore it was found that after completion of the self-assembly the binding reagent is not carried over the support into other reagent spots by the washing process. Furthermore it was found that the individual spatially defined zones are also stable after fabrication of the functionalized surfaces i.e. the adsorbed binding reagents remain at the same site and do not migrate to unoccupied sites on the metal or metal oxide surface.

The areas of the applied reagent spots preferably have a diameter of $\leq 5$ mm, preferably a diameter of $\leq 1$ mm. Reagent spots are most preferably applied in the micrometer range e.g. with a diameter of 50 to 500 $\mu$m. This corresponds to a dropwise added liquid volume of the reagent solution of about 0.1 to 10 nl. Since spatially sharply defined spots are obtained with the process according to the invention it is possible to produce a microarray structure. Different reactants or/and different reactant concentrations e.g. for immunological tests or nucleic acid hybridization tests can be applied to each of the individual spot zones.

A noble metal surface is a preferred surface and particularly preferably a gold or silver surface and most preferably a gold surface. Such a metal surface can for example be formed by vapour-depositing a thin metal layer on a support, for example a glass support. Such a vapour-deposited layer is preferably 10 to 100 nm thick. An SH or SS reagent is preferably used as the adsorptive binding reagent when using a noble metal surface. Such thiol and disulfide reagents are described in detail for example in DE 40 39 677. A compound containing a thiol or disulfide group is particularly preferably used as the adsorptive binding reagent which additionally contains a specifically bindable group such as e.g. an antigen, hapten or biotin group. Biotinylated thiol reagents adsorbed as an SAM to a surface can subsequently be coated with streptavidin, a different biotin content in different spots leading to different streptavidin layers.

However, it is also possible to use a metal oxide as the surface. Examples of suitable metal oxide surfaces are $SiO_2$, $TiO_2$, $Al_2O_3$, $Sn_2O_3$, $Ag_2O$, $La_2O_3$, $Ta_2O_5$ and mixtures thereof. A metal oxide surface composed of $SiO_2$ and/or $TiO_2$ is preferably used. If a metal oxide surface is used a compound containing a silane group is preferably used as the adsorptive binding reagent. Such compounds are described for example in EP-A-0 664 452. When compounds containing silane groups are adsorbed to metal oxide surfaces a covalent cross-linking for example by heating takes place after the adsorption.

The adsorptive binding reagents used according to the invention preferably contain, in addition to the respective adsorptive groups such as an SH, SS or silane group, at least one specifically bindable group such as biotin, a biotin derivative, streptavidin, a hapten, an antigen and/or a nucleic acid sequence which specifically bind to a binding partner e.g. to an analyte to be determined. The binding of analytes to a functionalized solid phase matrix according to the invention can for example be detected by confocal scanner fluorescence microscopy or by plasmon resonance spectroscopy. The detection is preferably carried out by means of plasmon resonance microscopy (B. Ruthenhäusler et al., Nature, vol. 332 (1988) 615–617). The binding of the analyte can be detected with surface plasmon resonance without using labelling reagents. The simultaneous determination of plasmon resonance and fluorescence detection is particularly preferably used to detect the binding of an analyte. In this case the plasmon resonance signal and the fluorescence signal are obtained independently of one another which also enables the determination of reaction kinetics in addition to a high sensitivity ($10^{-14}$ mol/l).

A further subject matter of the invention is a solid phase matrix comprising a support which is essentially continuously coated with a metal or metal oxide layer on which spatially defined reagent areas are arranged which (a) contain different solid phase reactants or/and (b) contain a solid phase reactant at different concentrations. Such a solid phase binding matrix preferably comprises at least three differently functionalized zones on a surface and particularly preferably at least 5 differently functionalized zones. The diameter of the reagent spots is preferably $\leq 5$ mm, more preferably $\leq 1$ mm and most preferably $\leq 500$ µm. Such a solid phase matrix with reagent spots in the µm range can also be called a microarray.

A further subject matter of the invention is a method for the detection of a binding or/and interaction of analytes in which a solid phase matrix according to the invention is used. If plasmon resonance spectroscopy or/and plasmon resonance microscopy is used as the detection method, a real time detection is possible and a label is not required since the layer thickness can be measured. Such a method can be used in molecular diagnostics to determine allergies, in immunology as well as for nucleic acid hybridization. A combination of plasmon resonance spectroscopy and fluorescence detection or a combination of plasmon resonance microscopy and fluorescence detection is particularly preferably used to detect the binding or/and interaction of the analyte.

Figure 3:
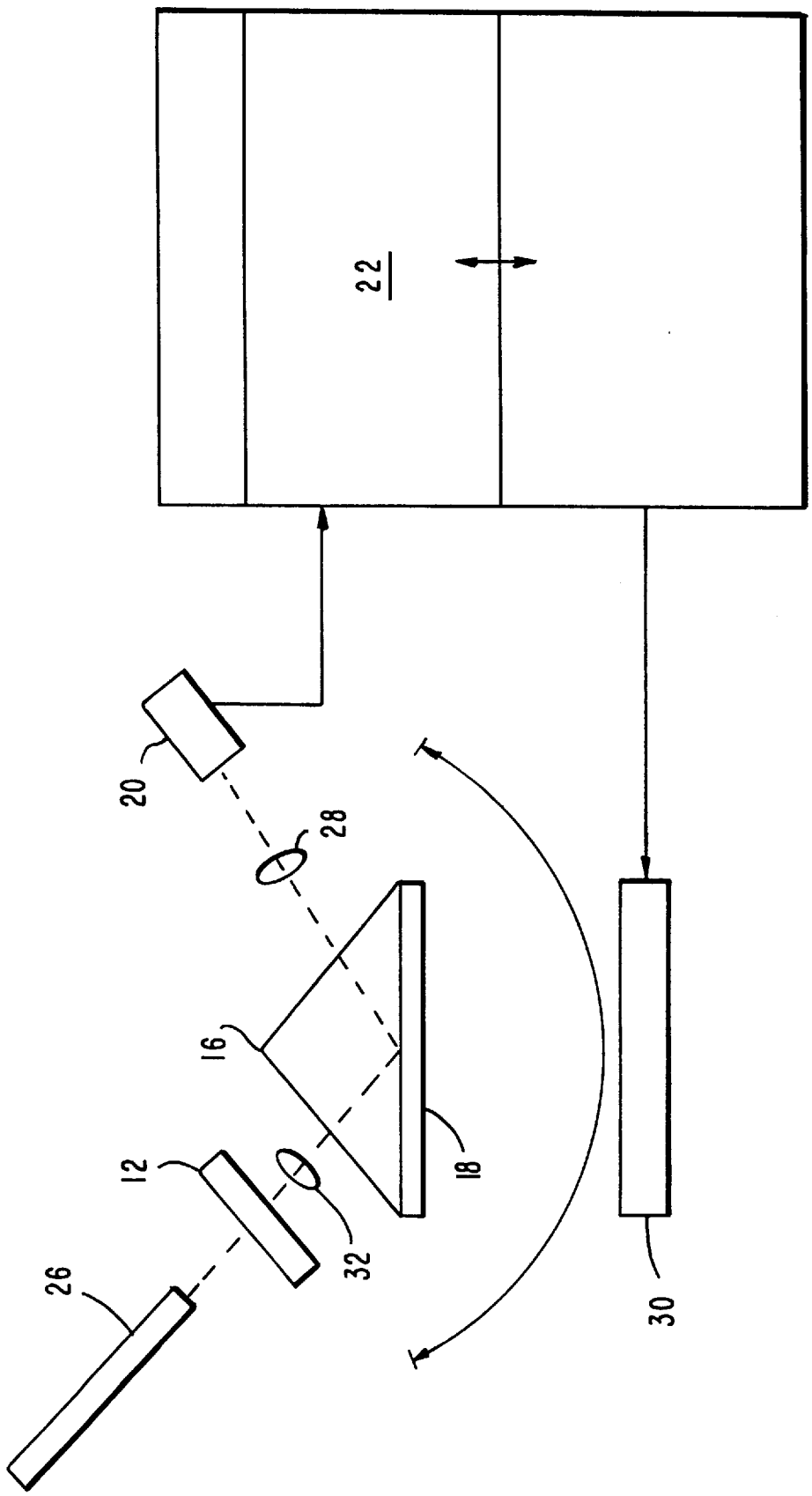
Figure 4A:
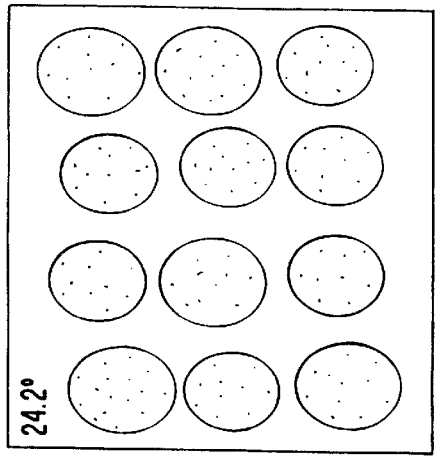
Figure 4B:
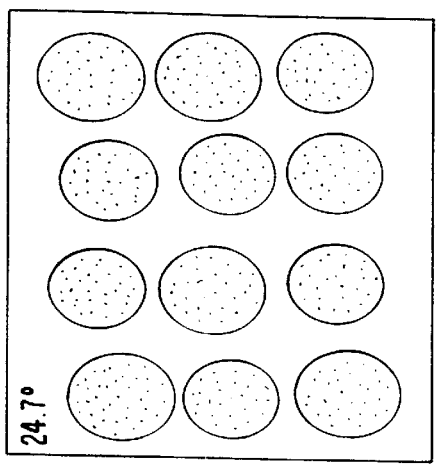
Figure 4C:
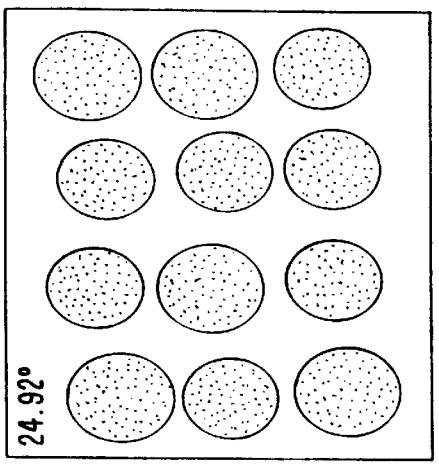
Figure 4D:
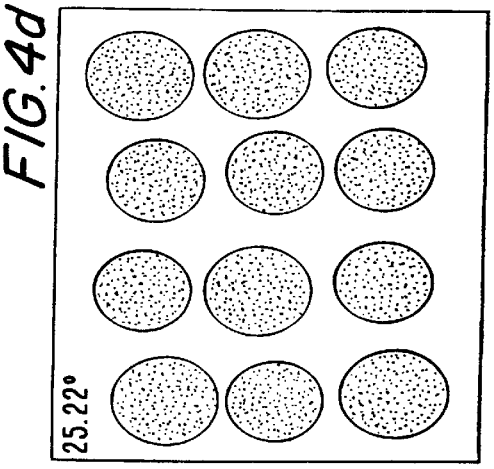
Figure 4E:
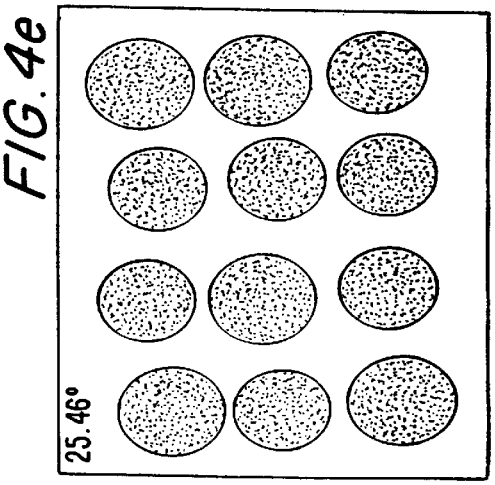
Figure 4F:
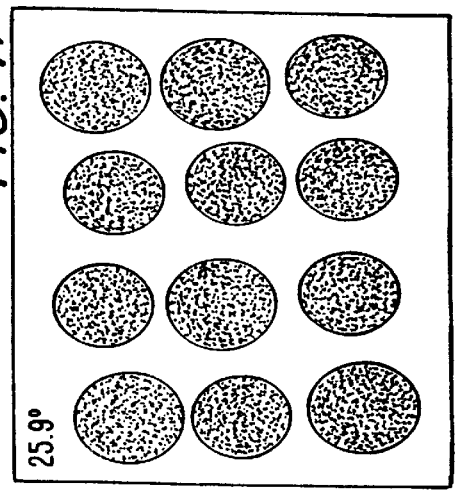
Figure 5A:
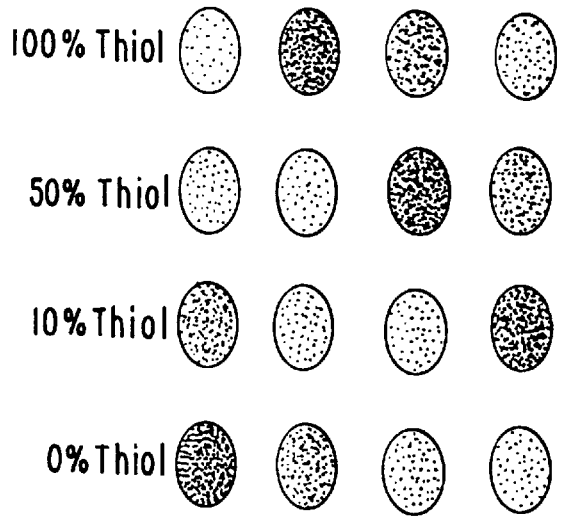
Figure 5B:
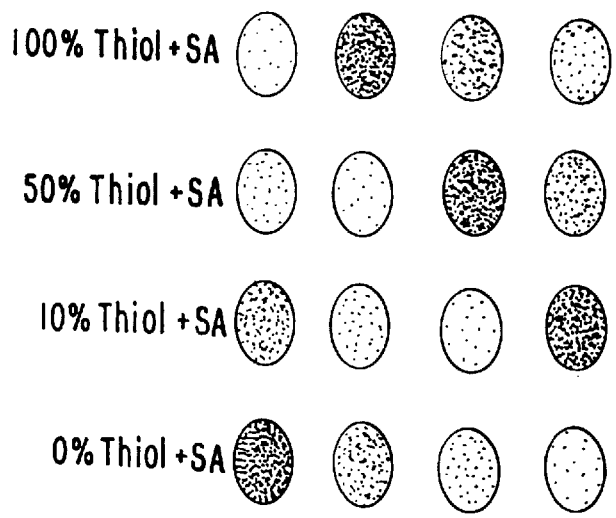

The invention is further elucidated by the attached figures and the following examples in which FIG. 1 illustrates the principle of applying the reagent spots, FIGS. 2a–d show reagents which are suitable for forming self-assembled monolayers, FIG. 3 shows the experimental construction of a surface plasmon microscope, FIGS. 4a–f show pictures obtained with a plasmon microscope of reagent spots applied according, to the invention to a gold surface and FIG. 5 shows the time-dependent reflection intensity versus time of a matrix with four different hydrophilic thiol mixtures obtained by surface plasmon microscopy.

EXAMPLE 1

Application of Reagent Spots to a Surface

The principle of the process according to the invention is elucidated by a preferred embodiment with reference to FIG. 1. Firstly a ca. 50 nm thick gold layer is vapour-deposited on a glass support made of LASFN9 high index glass in a high vacuum (ca. $10^{-7}$ mbar) with the aid of a high vacuum coating apparatus (Leibold Co.). Immediately after vapour-depositing the gold layer the support (10) is clamped on an XYZ table (Isel-EP 1090/4) (2) which is equipped with a silicon piezo pump (GeSIM, Dresden) (4). A microtitre plate (6) is also attached to the working surface of the XYZ table (2) which contains in the respective different wells the various adsorptive binding reagents to be applied dissolved in a solvent as well as the pure solvent. As substances for the adsorption a water-soluble thiol system composed of HS-Prop-DADOO-X-biotin (bindable reagent) (FIG. 2a) and HS-C2-aminoethoxy ethanol (diluent component) (FIG. 2b) was dissolved at a concentration of $5\times10^{-4}$ molar in water and an ethanol-soluble thiol system composed of HS-C12-DADOO-biotin (bindable biotin component) (FIG. 2c) and mercaptoundecanol (diluent component) (FIG. 2d) was dissolved at a concentration of $5\times10^{-4}$ molar in ethanol. These systems were placed in different wells of the microtitre plate at different mixing ratios with a proportion of biotin component of 0%, 10%, 50% and 100%. In order to apply reagent spots to the gold surface the tip of the pump (4) was now dipped into the corresponding liquid and then driven to the programmed position on the gold coated surface where a drop with a volume of ca. 1 nl (8) is deposited. Afterwards the pump is rinsed twice with pure solvent and the process is repeated with the next solution, the next spot being deposited at a distance of ca. 600 µm from the previous spot. This process can be repeated as often as desired.

Subsequently the gold surface on which the reagent spots have been applied is allowed to set for ca. 10 min during which a self-assembled monolayer forms on the surface covered with the drop. Subsequently the gold surface is rinsed over its entire area with a pure solvent in order to wash away non-adsorbed molecules. In this manner it is possible to produce surfaces with spatially defined reaction spots within a short period. The diameter of the spots is ca. 200 µm.

EXAMPLE 2

Plasmon Microscopic Examination of the Reagent Spots Applied to a Gold Surface

In order to determine the optical layer thicknesses of the prepared biotin monolayers and in order to examine the binding property towards streptavidin, the gold surface prepared with reagent spots was examined with the aid of surface plasmon microscopy in the Kretschmann configuration (prism coupled). In this process, as shown in FIG. 3 surface plasmons are excited through a prism (16) made of high-refraction glass at a specific angle of incidence on the metal layer (18) by widened laser light (red He—Ne laser) (14) that is p-polarized through a polarizer (12). The reflected light is recorded by a CCD camera (20) in relation to the angle of incidence. In addition the construction shown in FIG. 3 includes a goniometer (30) as well as two lenses (28, 32) which form the microscope optics. Different layer thicknesses on the reagent spots result in different light-dark contrasts on the recorded picture. With the aid of image analysis systems (22) comprising a computer it is possible to determine the absolute increase in the layer thickness as well as its time course with an accuracy of ca. 0.1 nm. FIG. 4 shows the pictures obtained by means of the CCD camera of the spots coated with thiol before and after streptavidin binding. FIG. 5 shows the time course of the intensities obtained by image analysis of streptavidin binding to differently coated spots. Six pictures are shown in FIG. 4a which each show 12 identically functionalized thiol spots at different angles of incidence of the laser light. A coated support with 16 reagent spots is shown in FIG. 4b in which case sets of 4 spots have the same functionalization, the left picture having been taken before the binding of streptavidin, the right-hand picture having been taken after the binding of streptavidin. As can be clearly seen the process according to the invention enables spatially separate, differently functionalized reagent spots to be applied to a continuous surface.

Figure 6:
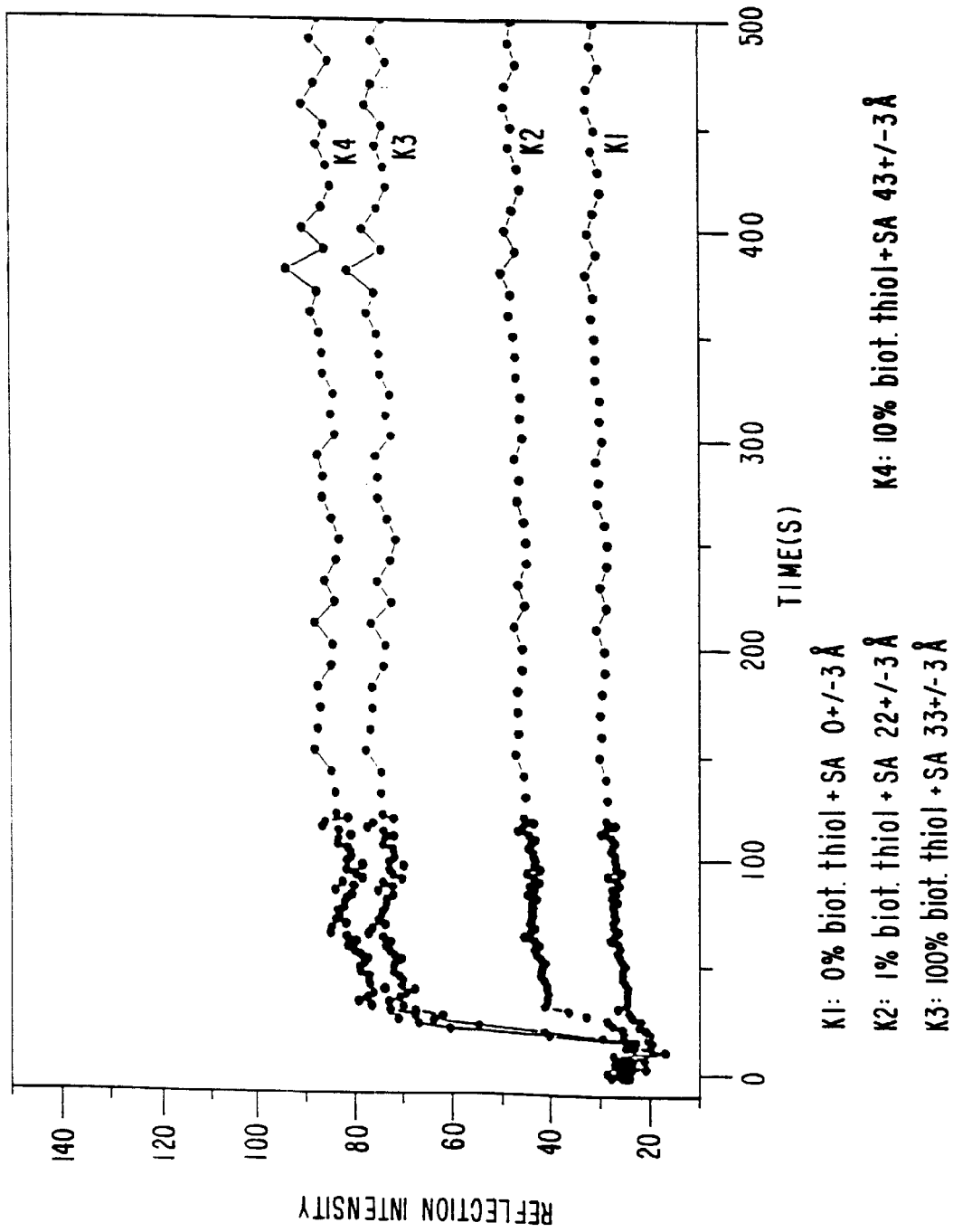

FIG. 5 shows the time course of the adsorption of streptavidin to a surface coated with four different hydrophilic thiol mixtures obtained by analysing the reflection intensity of the plasmon resonance microscopy. K1 represents a reagent spot on which a pure solvent solution was incubated. This spot was subsequently treated with streptavidin. As shown in FIG. 5 there is only a very slight binding of streptavidin to the reagent spot. K2 represents a reagent spot which was incubated with a solution composed of 1% biotinylated thiol and 99% diluent thiol and subsequently treated with streptavidin. It can be seen that there is a considerably higher streptavidin binding than in curve K1. K3 represents a reagent spot that was incubated with 100% biotinylated thiol, i.e. without diluent molecules, and subsequently treated with streptavidin. There is a considerable increase in the layer thickness to 33±3 Å compared to K2 where the layer thickness was 22±3 Å. Finally K4 represents a reagent spot which was treated with 10% biotinylated thiol and 90% diluent molecules. In this case a dilute homogeneous binding layer is formed which has the highest reflection after treatment with streptavidin from which a layer thickness of 43±3 Angström can be calculated. As shown in FIG. 6 reagent spots with different coatings can be applied to a single flat gold support resulting in the formation of an array system. In addition it is possible using such an array to detect bindings or/and interactions of analytes in which the layer thickness (coating amount) as well as the reaction kinetics (adsorption rate) can be determined.

What is claimed is:

1. A process for applying a spatially defined reagent area to a solid phase having an essentially continuous metal or metal oxide surface to form a solid phase matrix, comprising applying droplets of a liquid containing an absorptive binding reagent and at least one of a) different solid phase reactants and b) solid phase reactants at different concentrations to a solid phase having an essentially continuous metal or metal oxide surface for an adequate time period to enable formation of absorptive bonds between the binding reagent and to form a solid phase matrix, said matrix having at least one spacially defined reagent area thereon, wherein said at least one spacially defined reagent area contains at least one of a) different solid phase reactants and b) solid phase reactants at different concentrations.

2. A process of claim 1, wherein said solid phase matrix comprises at least three differently functionalized spacially separated reagent areas from one another on said continuous metal or metal oxide layer.

3. A process of claim 1, wherein the reagent area has a diameter of less than or equal to 5 mm.

4. A process of claim 1, wherein the reagent area has a diameter of less than or equal to 1 mm.

5. A process of claim 1, wherein said surface is metal.

6. A process of claim 5, wherein the metal surface comprises at least one metal selected from the group consisting of gold and silver.

7. A process of claim 5, wherein the absorptive binding reagent is a compound containing either a thiol or disulfide group.

8. A process of claim 1, wherein the surface is a metal oxide.

9. A process of claim 8, wherein the absorptive binding reagent is a compound having a silane group.

10. A process of claim 1, wherein the adsorptive binding reagent is applied as a self-assembled monolayer.

11. A process of claim 10, wherein the adsorptive binding reagent is applied as a homogeneous laterally diluted monolayer.

* * * * *